(12) United States Patent
Melchionne et al.

(10) Patent No.: US 12,027,264 B2
(45) Date of Patent: Jul. 2, 2024

(54) MEDICAL INTERVENTION BASED ON SEPARATE DATA SETS

(71) Applicant: International Business Machines Corporation, Armonk, NY (US)

(72) Inventors: John Melchionne, Kingston, NY (US); Michael Amisano, East Northport, NY (US); John Behnken, Hurley, NY (US); Jeb R. Linton, Manassas, VA (US); David K. Wright, Monroe, MI (US); Dennis Kramer, Siler City, NC (US)

(73) Assignee: International Business Machines Corporation, Armonk, NY (US)

( * ) Notice: Subject to any disclaimer, the term of this patent is extended or adjusted under 35 U.S.C. 154(b) by 615 days.

(21) Appl. No.: 16/792,708

(22) Filed: Feb. 17, 2020

(65) Prior Publication Data

US 2021/0257088 A1 Aug. 19, 2021

(51) Int. Cl.
*G16H 10/60* (2018.01)
*G16H 40/67* (2018.01)
*G16H 50/20* (2018.01)

(52) U.S. Cl.
CPC ............ *G16H 40/67* (2018.01); *G16H 10/60* (2018.01); *G16H 50/20* (2018.01)

(58) Field of Classification Search
CPC ......... G16H 40/67; G16H 10/60; G16H 50/20
See application file for complete search history.

(56) References Cited

U.S. PATENT DOCUMENTS

| 6,421,650 | B1 | 7/2002 | Goetz et al. |
| 7,181,017 | B1 | 2/2007 | Nagel et al. |
| 7,900,052 | B2 | 3/2011 | Jonas |
| 9,031,853 | B2 | 5/2015 | Bartfeld et al. |
| 9,177,265 | B2 | 11/2015 | Bartfeld et al. |

(Continued)

FOREIGN PATENT DOCUMENTS

CN 105303113 B 8/2018

OTHER PUBLICATIONS

Jahan et al., "Design of a Secure Sum Protocol using Trusted Third Party System for Secure Multi-Party Computations," 2015 6th International Conference on Information and Communication Systems (ICICS), Apr. 7-9, 2015, IEEE, pp. 136-141.

(Continued)

*Primary Examiner* — Stella Higgs
*Assistant Examiner* — Aaisha Abdullah
(74) *Attorney, Agent, or Firm* — Eric W. Chesley (57) ABSTRACT

A first patient intervention is identified. The first patient intervention regards a first patient record that includes one or more attributes related to a first patient. The first patient intervention is transmitted to a first program split of a secure multi-party computation. A conflict is detected in the first patient intervention and an existing medical situation regarding the first patient. The conflict is detected by the first program split of the secure multi-party computation and by a third program split of the secure multi-party computation. Based on the detected conflict, a notification is generated by the first program split. The notification is based on the detected conflict. The notification based on the detected conflict is provided to a first client.

19 Claims, 5 Drawing Sheets

(56) References Cited

U.S. PATENT DOCUMENTS

| | | |
|---|---|---|
| 9,197,637 B2 | 11/2015 | Sy et al. |
| 9,419,951 B1 | 8/2016 | Felsher et al. |
| 9,648,021 B2 | 5/2017 | Tsai |
| 9,729,525 B1 | 8/2017 | Kolman et al. |
| 9,996,607 B2 | 6/2018 | Alexe et al. |
| 10,127,289 B2 | 11/2018 | Manning et al. |
| 10,515,625 B1 | 12/2019 | Metallinou et al. |
| 10,614,242 B2 | 4/2020 | Rogers et al. |
| 10,628,483 B1 | 4/2020 | Rao et al. |
| 10,691,825 B2 | 6/2020 | Jones et al. |
| 2004/0210763 A1 | 10/2004 | Jonas |
| 2009/0282039 A1 | 11/2009 | Diamond |
| 2013/0238360 A1* | 9/2013 | Bhathal ............... G16H 20/10 705/3 |
| 2014/0303988 A1* | 10/2014 | Maneri ............... G16H 50/20 705/2 |
| 2015/0213079 A1* | 7/2015 | Shukla ............... G06F 16/2365 707/687 |
| 2015/0220588 A1 | 8/2015 | Krauss |
| 2016/0012195 A1 | 1/2016 | Lee |
| 2016/0078446 A1 | 3/2016 | Trostle |
| 2016/0085938 A1 | 3/2016 | Hans |
| 2016/0117446 A1* | 4/2016 | Hussam ............... G16H 10/60 705/3 |
| 2016/0125067 A1 | 5/2016 | Alexe et al. |
| 2016/0205114 A1 | 7/2016 | Yan |
| 2016/0210427 A1* | 7/2016 | Mynhier ............... G16H 10/60 |
| 2017/0039342 A1* | 2/2017 | Nichols ............... G16H 70/40 |
| 2017/0364595 A1 | 12/2017 | Desai et al. |
| 2018/0060508 A1* | 3/2018 | Fokoue-Nkoutche ............... G16H 15/00 |
| 2018/0096166 A1 | 4/2018 | Rogers et al. |
| 2018/0139045 A1 | 5/2018 | Furukawa et al. |
| 2018/0276417 A1 | 9/2018 | Sanchez |
| 2018/0322946 A1* | 11/2018 | Ika ............... G06F 21/6254 |
| 2018/0357434 A1 | 12/2018 | Roy |
| 2018/0367293 A1 | 12/2018 | Chen et al. |
| 2019/0005019 A1* | 1/2019 | Burke ............... G06F 40/284 |
| 2019/0108899 A1* | 4/2019 | Robkin ............... G16H 50/20 |
| 2019/0245705 A1 | 8/2019 | Kumar et al. |
| 2019/0286837 A1 | 9/2019 | Yim et al. |
| 2019/0303371 A1 | 10/2019 | Rowe et al. |
| 2019/0378599 A1 | 12/2019 | Amisano et al. |
| 2020/0007514 A1* | 1/2020 | Li ............... G06F 21/6245 |
| 2020/0184100 A1 | 6/2020 | Ong et al. |
| 2020/0211105 A1 | 7/2020 | Du |
| 2020/0226284 A1 | 7/2020 | Yin et al. |
| 2020/0327250 A1* | 10/2020 | Wang ............... G16B 50/40 |
| 2021/0051007 A1 | 2/2021 | Li et al. |
| 2021/0051008 A1 | 2/2021 | Li et al. |
| 2021/0373937 A1* | 12/2021 | Veeningen ............... G06F 9/5066 |

OTHER PUBLICATIONS

Kumar et al., "A critical review on application of secure multi party computation protocols in cloud environment," International Journal of Engineering & Technology, 7 (2.7), 2018, pp. 363-366. (Year: 2018).

Pal et al., "Designing an Algorithm to Preserve Privacy for Medical Record Linkage with Error-Prone Data," JMIR Medical Informatics 2014, vol. 2, Issue 1, 18 pages. (Year: 2014).

Vatsalan et al., "Multi-Party Privacy-Preserving Record Linkage using Bloom Filters," arXiv: 1612.08835v1 [cs. DB], Dec. 28, 2016, 13 pages. (Year: 2016).

Anonymous, "Securing Supply Chain Interactions in Regulatory Domain Translation<br /><br />," IP.com Prior Art Database Technical Disclosure, IP.com No. IPCOM000255461D, Sep. 27, 2018, 6 pages. https://ip.com/IPCOM/000255461.

Anonymous, "Method and System for Offering Alternative Drugs to limit Over Prescribing of Antibiotics Using Cognitive Techniques," IP.com Prior Art Database Technical Disclosure, IP.com No. IPCOM000250710D, Aug. 25, 2017, 5 pages. https://ip.com/IPCOM/000250710.

Anonymous, "Blockchain/Cognitive Technology Platform as an Adviser to Support Pharmacy Operations: Drug Use Management and Drug Inventory Management," IP.com Prior Art Database Technical Disclosure, IP.com No. IPCOM000249234D, Feb. 10, 2017, 5 pages. https://ip.com/IPCOM/000249234.

Hammer, T., "eMedication—improving medication management using information technology," Linnaeus University Dissertations, Doctoral Disseration, No. 188/2014, Oct. 2014, 77 pages.

Kirking et al., "Detecting and Preventing Adverse Drug Interactions: The Potential Contribution of Computers in Pharmacies," Soc. Sci. Med., vol. 22, No. 1, pp. 1-8, 1986, Pergamon Press Ltd.

Wang et al., "SCORAM: Oblivious RAM for Secure Computation," CCS '14: Proceedings of the 2014 ACM SIGSAC Conference on Computer and Communications Security, Nov. 2014, 12 pages.

Singha et al., "A Review on Security and Privacy Challenges of Big Data", Cognitive Computing for Big Data Systems Over IoT, First Online: Dec. 31, 2017, 11 pages.

Vatsalan et al., "A taxonomy of privacy-preserving record linkage techniques", Information Systems, SciVerse ScienceDirect, Nov. 2012, 24 pages.

Du et al., "Secure Multi-Party Computation Problems and Their Applications: A Review and Open Problems", In Proceedings of the 2001 Workshop on New Security Paradigms, ACM, Sep. 2001, 10 pages.

Mell et al., "The NIST Definition of Cloud Computing", Recommendations of the National Institute of Standards and Technology, Special Publication 800-145, Sep. 2011, 7 pages.

Kramer et al., "Secure Data Monitoring Utilizng Secure Private Set Intersection", U.S. Appl. No. 16/203,830, filed Nov. 29, 2018.

Linton et al., "Entity Resolution Between Multiple Private Data Sources," U.S. Appl. No. 16/449,666, filed Jun. 24, 2019.

List of IBM Patents or Patent Applications Treated as Related, Signed Feb. 17, 2020, 2 pages.

\* cited by examiner

MEDICAL INTERVENTION BASED ON SEPARATE DATA SETS

BACKGROUND

The present disclosure relates to medical interventions, and more specifically, to guiding medical interventions based on secure multi-party computation against private data.

Medical interventions may operate based on a dataset located within the care and possession of a medical provider. Patients may in some situations access medical care and treatment from multiple providers. Each provider may only be able to operate with a limited set of data, which can slow or impair the ability to provide care to patients.

SUMMARY

According to embodiments disclosed are a method, system, and computer program product. A first patient intervention is identified. The first patient intervention regards a first patient record that includes one or more attributes related to a first patient. The first patient intervention is transmitted to a first program split of a secure multi-party computation. A conflict is detected in the first patient intervention and an existing medical situation regarding the first patient. The conflict is detected by the first program split of the secure multi-party computation and by a third program split of the secure multi-party computation. Based on the detected conflict, a notification is generated by the first program split. The notification is based on the detected conflict. The notification based on the detected conflict is provided to a first client.

The above summary is not intended to describe each illustrated embodiment or every implementation of the present disclosure.

BRIEF DESCRIPTION OF THE DRAWINGS

The drawings included in the present application are incorporated into, and form part of, the specification. They illustrate embodiments of the present disclosure and, along with the description, serve to explain the principles of the disclosure. The drawings are only illustrative of certain embodiments and do not limit the disclosure.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION

Aspects of the present disclosure relate to medical interventions, and more specifically, to guiding medical interventions based on secure multi-party computation against private data. While the present disclosure is not necessarily limited to such applications, various aspects of the disclosure may be appreciated through a discussion of various examples using this context.

Patient medical interventions (patient interventions) may be a process by which healthcare providers attempt to modify the outcome of a patient's health or well-being. Healthcare providers, such as nurses, doctors, dentists, pharmacists, and the like may operate to treat or cure a condition of the patient. Each of the healthcare providers may provide a patient intervention in the form of a treatment, such as a surgical procedure, a massage, or physical therapy. A patient intervention may be the assignment to the patient of a regime of specific exercises or movement, or to cease an existing exercise or movement. A patient intervention may be in the form of a modification of a certain portion of a patient's diet, such as the addition of food, or the removal of a certain drink. A patient intervention may be in the form of prescribing a certain drug or medication to be taken by a patient at a certain time or at a specific time interval.

Each healthcare provider may be limited in the scope of knowledge about a patient (e.g., the information about any prior diagnosis of the patient, and the information about the patient's existing or past interventions). For example, certain laws or regulations, such as the Health Insurance Portability and Accountability Act (HIPAA) may require the safeguarding of patient data. These laws may prevent healthcare providers from disclosing, sharing, or otherwise making available any information, including patient interventions. For example, a patient may have a multitude of conditions or diagnosis. In another example, a patient may currently be prescribed a certain medication. In some examples, a patient may have exhibited a drug-seeking behavior.

This patient information and other attributes (e.g., age, name, familial relations) may be stored across many different databases controlled by various medical providers (clients). Each of the clients may or may not have the ability to share or even link this information for use by other healthcare providers. In some scenarios, healthcare providers may not be able to even acknowledge that they have seen a particular patient. This can lead to a dangerous situation for a patient if conflicting or otherwise incompatible patient interventions are prescribed by differing healthcare providers. Avoidance of drug interactions can be imperative for improving patient care and for ensuring healthcare outcomes are achieved expediently without creating unnecessary complications.

Consequently, a technological solution that enables the detection of conflicts between patient interventions held in two or more private data sets may be useful. One possible solution is using a multi-party conflict detection. For example, two healthcare providers may wish to compare information about a first patient, from two data sources that are controlled by the two providers, respectively. Due to privacy requirements, neither of the healthcare providers may share the patient records between each other and may not consequently be able to identify any conflicts with the interventions that they are providing to a given patient. Certain private conflict detection techniques may be helpful but may be limited in scope.

Specifically, private conflict detection techniques can only identify an exact match between two records of a patient. This may be of limited usefulness when dealing with patient records. There are many drawbacks to exact match identification. First, data is not always identical between two different healthcare providers. In many cases, data may differ. There are situations where users that are responsible for entering data may misspell attributes, values, words, or make grammatical mistakes. Sometimes, the names of individuals are spelled in an atypical fashion and the average data entry user may not enter that information properly. Sometimes, different organizations use shorthand or other abbreviations when referring to certain attributes. For example, a given intervention may have a different name or acronym depending on the healthcare provider. In another example, these acronyms may refer to the same patient, or a different patient. In some scenarios, data may be purposefully entered improperly, when individuals enter forms with partial truths or omissions. Sometimes, data in two data sets may not match because the technology fails, such as when bit rot or other data corruption occurs in one or more parties' data. Other more benign issues may occur: records that are out of date; records that have simple case, punctuation, or spacing differences. In each of these cases, private conflict detection techniques would not identify when two data-sets are matching.

Further, existing private conflict detection techniques cannot deal with more complex relationship detection between various patient records. Attributes stored about a patient may include their name, birthday, and previous addresses. Other records may also include information regarding other individuals related to the patient, such as family members. In a third example, patients may have a relationship, such as a mother and child. However, private conflict detection techniques may not be able to detect the relationships between the patient and other patients in these examples. A valuable record about a prescription allergy and a genetic connection between two patients may not be identified because existing private conflict detection techniques may only match patient records that are of the same patient.

A method of searching two datasets that may yield improvements is entity resolution. Entity resolution and relationship detection (entity relation operations) may be performed by a set of rules (e.g., a predetermined set of rules). The rules may function to determine when entries in two data sets refer to the same individual or refer to two individuals with a relationship. For example, a system using such a search model may decide that J. Smith and John Smith, with the same phone number, are the same person; whereas J. Smith and Alice Smith, with the same street address, are two individuals with a relationship. The drawback to this system is that—so far—private medical data may not be used in conjunction with entity-relation operations. Rather, entity-relation operations may require that the data of multiple datasets be digested, analyzed, in some cases reorganized. Further, entity-relation operations may require that evaluations are performed, and rules are validated against many, or all, other entity records. The laws and regulations around healthcare may not allow for these data sets of patient records to be shared, viewed, or otherwise intermingled—consequently, entity resolution and relationship detection may not be performed, as of yet, on patient data.

Embodiments of the disclosure may provide for Private Healthcare Patient Intervention Conflict Detection (PHPICD) by placing all of the data from two parties within a secure data store. Further, the secure data store of the PHPICD may only be accessed in a coordinated fashion through a secure multi-party computation (SMPC) (alternatively, multi-party computation). The SMPC may operate through two or more SMPC programmatic splits. The PHPICD system may function as a SMPC using one or more relevant techniques, such as Yao Construct Garbled Circuit pair. In some embodiments, SMPC may leverage the use of one or more of the following techniques: Yao Construct Garbled Circuits, Shamir Secret Sharing, Additive Secret Shares, and/or Partially Homomorphic Encryption. This may allow full featured entity resolution and relationship detection to be performed through a cooperative computation between two healthcare providers (e.g., through the programmatic splits) without requiring either organization to reveal their input data. The operations of the SMPC may provide a zero knowledge system of performing conflict detection of various patient interventions (e.g., revealing only the absolute minimum information needed to perform a task, without leaking any other information). The operations of the SMPC may not be able to be performed without all splits. For example, an SMPC operating with two program splits may include a first split and a second split. The first split of the program splits may be unable to perform operations without the second split. Further, the second split of the program splits may be unable to perform operations without the first split. In some embodiments, the output may be revealed at the end of the computation to either or both organizations.

In some embodiments, a Three-Party Computation variant of SMPC within secure data store may occur, in which the first and second parties are organizations with an interest in detecting entity overlaps and relationships in their private data. The third party in the secure computation may be a Cloud-based Server which houses the secure data store.

In some embodiments, a Two-Party Computation variant of SMPC within a secure data store may occur. Two parties to the Two-Party Computation variant include two organizations with an interest in detecting entity overlaps and relationships in their private data. One of the two parties may agree also to host the secure data store. Security in embodiments where one party hosts the secure data store is equivalent to other embodiments through the secure data store. Specifically, the party hosting the data stored in the secure data store still cannot meaningfully inspect the data or the data access operations.

In some embodiments, computation of an SMPC may involve having three or more organizations access a common shared system which is housed in a cloud-based server. The data cooperatively stored in the secure data store may be encrypted by way of a split key. The split key may use a technique for allowing a subset of parties to access the secure data store, such as Threshold Secret Sharing. Consequently, as long as a required threshold of participants cooperates to perform multi-party computations, the SMPC can recreate the keys needed to decrypt the data in the secure storage. For example, an SMPC may be created with five splits that are each controlled by five parties, one of which may host private data for the five parties. The split key may require that four of the five parties cooperatively operate to perform entity resolution/relationship detection.

Figure 1:
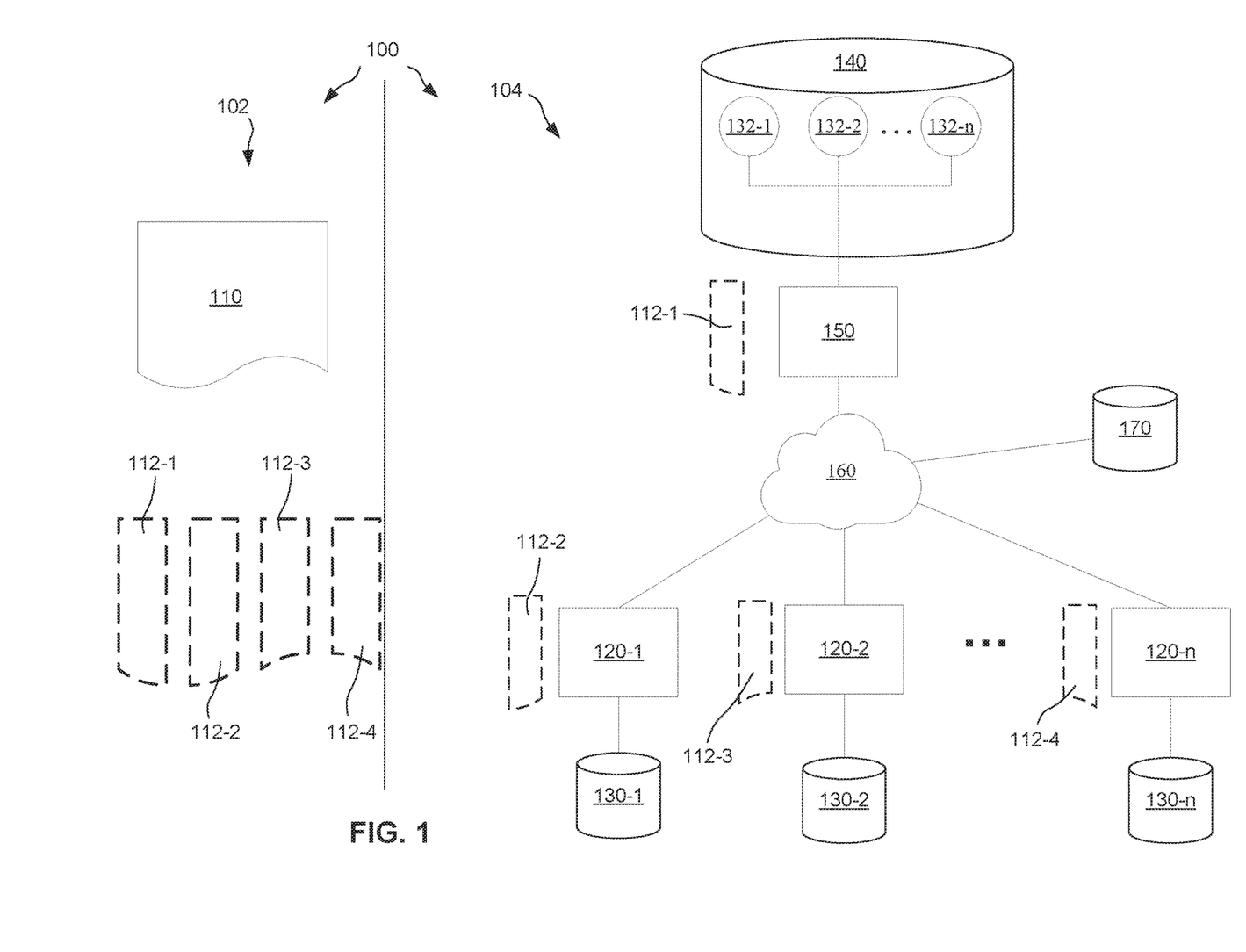
FIG. 1 depicts an example Private Patient Healthcare Intervention Conflict Detection System, consistent with some embodiments of the disclosure.

FIG. 1 depicts an example Private Patient Healthcare Intervention Conflict Detection System (PHPICD) 100, consistent with some embodiments of the disclosure. The PHPICD 100 may permit analysis and enable parties to learn about relationships between records in their own private data sets and the records in other private datasets. The PHPICD 100 may enable the detection of a conflict in patient interventions between multiple datasets of patient records without any private data or patient records being accessed by any individual party. The PHPICD may leverage entity resolution and relationship detection (entity-relation operations). The PHPICD may provide only a notice that a conflict in a patient intervention is present with other existing patient interventions.

At a time 102, a program designed to perform one or more operations of system 100 may be compiled into a program 110. During compilation, at 102, the program 110 may be compiled into splits 112-1, 112-2, 112-3, 112-4 (collectively, 112). Each of the splits 112 may be operable by one or more clients or servers of system 100. The number of splits 112 may correspond to the number of clients and servers of a given PHPICD 100. For example, in an embodiment having seven clients and one server, there may be eight splits 112 of program 110. The system 100 may operate at a time 104. Time 104 may be after time 102.

Figure 3:
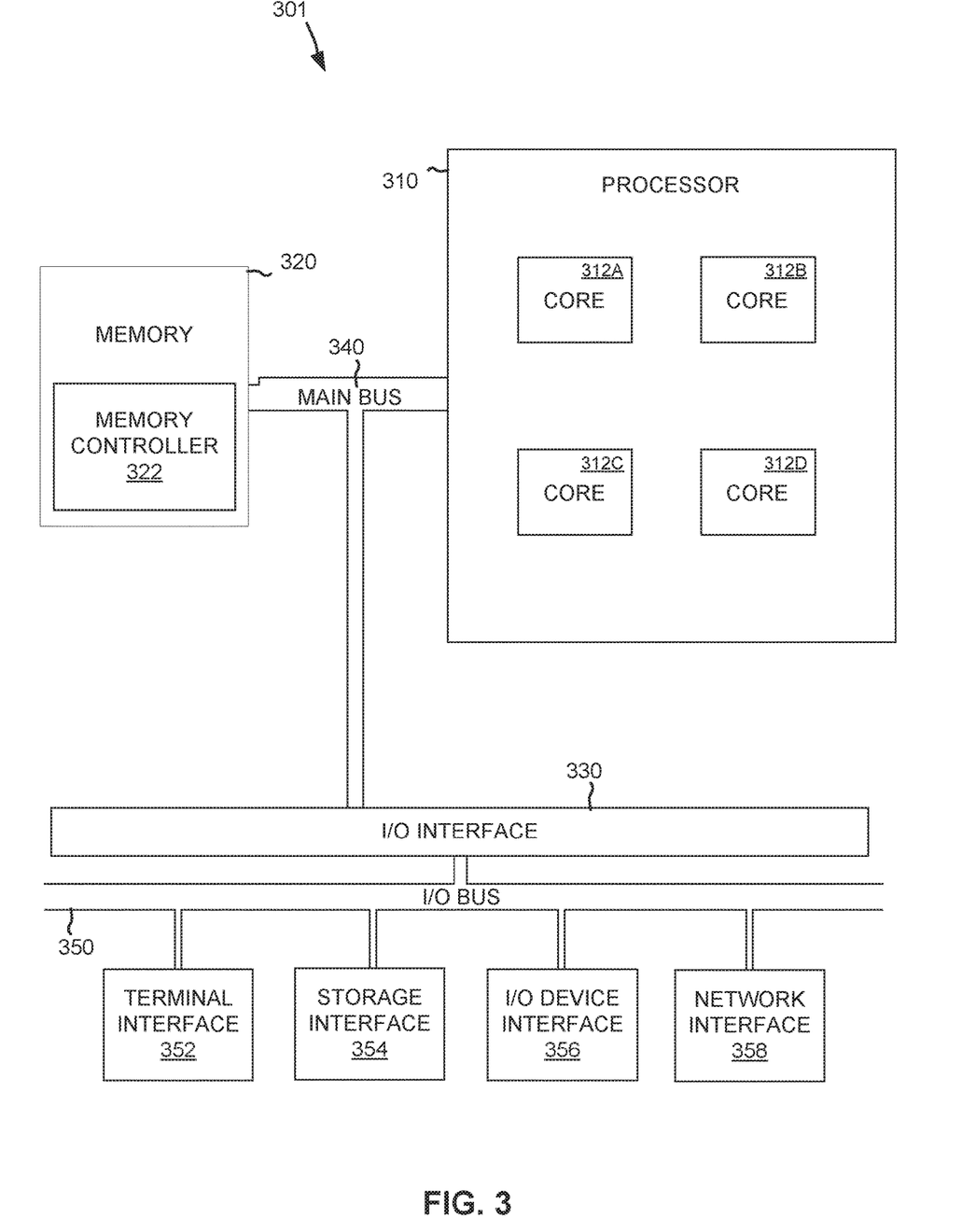
FIG. 3 depicts the representative major components of an example computer system that may be used, in accordance with some embodiments of the present disclosure.

The system 100 may include the following: multiple clients 120-1, 120-2, to 120-n (collectively, 120); a secure data store 140; a server 150 for processing of requests to the secure data store; and a network 160 for communicatively connecting the other components of the system. Network 160 may be a network or collection of networks, including a local area network (LAN), or a wide area network, such as, the Internet. The clients 120 may be one or more computer systems or servers (and associated software) configured to receive and process requests, to host users, and to execute a split of program 110 for conflict detection. For example, FIG. 3 depicts an example computer system 301 capable of operating as a client 120 consistent with some embodiments. Each of the clients 120 may be operated or controlled by healthcare providers. For example, a first healthcare provider may own, operate, and control client 120-1, and a second healthcare provider may own, operate, and control client 120-2.

Referring back to FIG. 1, the clients 120 may each have a private data store that houses data collected and retained by a party. For example, a first party operates client 120-1 and stores and retrieves data from private data store 130-1. A second party operates client 120-2 and stores and retrieves data from private data store 130-2. Respectively, additional parties operate additional clients and store and retrieve data from other private data stores. For example, an nth party operates client 120-n and stores and retrieves data from private data store 130-n. The private data stores (collectively 130) (alternatively, other data stores) may be a database, linked list, or other data structure designed to store and retrieve records.

In some embodiments, each client 120 may be under the control of or operate under a single party. For example, a first entity affiliated with a first medical provider may be a first party fully in ownership and control of client 120-1. The first entity may own and control data as part of its normal course of operation to provide care for patients by retaining records in private data store 130-1. A second entity affiliated with one or more second additional healthcare providers may be a second party fully in ownership and control of client 120-2. The second entity may possess and/or control data as part of its normal course of operation to provide care for patients by retaining records in private data store 130-2. In such case, clients 120-1 and 120-2 (and private data stores 130-1 and 130-2, respectively) may be located geographically distant from each other.

In some embodiments, client 120-1 may not access any other data located in other data stores 130 other than data store 130-1. Likewise, client 120-2 may not access any other data located in other data stores 130 other than data store 130-2. The inability to access other records from other datastores may be due to a regulation, such as a healthcare record regulation that forbids the accessing of records held by other healthcare providers. The inability to access other records may be due to a technical reason. For example, client 120-2 may not have network connectivity to data store 130-1; client 120-2 may be technically incapable of retrieving, viewing, or otherwise accessing healthcare records of patients stored in data store 130-1.

In some embodiments, multiple parties may be assigned to operate a given client 120. For example, a client 120 may include an authentication and access management system that would enable multiple separate organizations to operate client 120. Enabling multiple separate organizations to operate client 120 may enable multi-tenancy without adding to the computational and architectural complexity of program 110. To provide for multi-tenancy, some embodiments may include distributing the same software to multiple parties and hosting multiple copies of a given client 120 (e.g., through virtual machines). In some embodiments, the distributed software may include time sharing access to a given client 120.

To ensure privacy between multiple parties in embodiments involving sharing a given client 120, data may be labeled and isolated in a given private data store 130. For example, a first party may log into client 120-2 and insert records into private data store 130-2. Upon insertion, client 120-2 may scramble, or otherwise obfuscate the records of the first party before storing those records into private data store 130-2. A second party may also log into client 120-2 (with differing credentials) and insert records into private data store 130-2. Upon insertion, client 120-2 may scramble, or otherwise obfuscate the records of the second party before storing those records into private data store 130-2. All of the records stored in private data store 130-2 may also include a tenant/owner label corresponding to each party. Client 120-2 may operate based on a relevant access control mechanism to only allow the first party and second party access only to their own records and not the records of the other.

Secure data store 140 may be a database, linked list, or other data structure designed to store and retrieve records. In some embodiments, secure data store 140 may operate such that any party cannot discern any meaning regarding the secure data store. For example, client 120-1 may be configured to host secure data store 140. Secure data store 140 may operate such that the insertion, organization, deletion, or other modification of records is opaque to inspection by client 120-1.

Secured data store 140 may utilize one or more techniques of oblivious storage. Secure data store 140 may operate in the form of Oblivious Random Access Memory (ORAM). ORAM can be thought of as a database that can run on an untrusted server, where the read and write operations are controlled by and visible to a client, but the operations are completely opaque to the server. Secure data store 140 may also operate as a working memory for hosting of one or more programs. In some embodiments, server 150, or one or more splits 112 of program 110 may be executed within secure data store 140. This may ensure that only authenticated clients have access to the operations and functioning of program 110—and the programmatic splits 112 of the program—without any party that hosts secure data store 140 able to discern any meaning of the data and operations within the secure data store.

Figure 5:
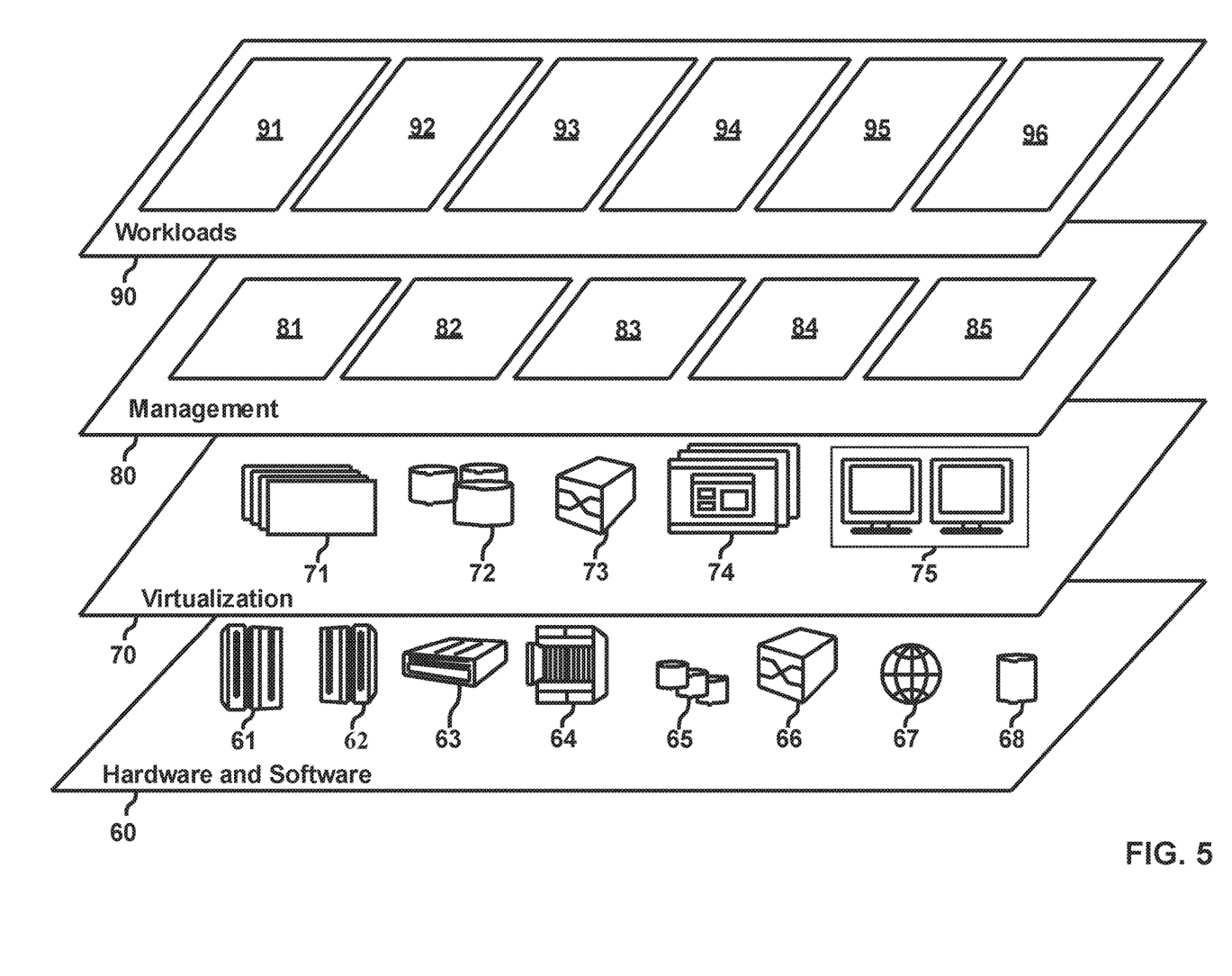
FIG. 5 depicts abstraction model layers according to an embodiment of the present invention.

Server 150 may be a single computer system configured to perform one or more operations of system 100. For example, FIG. 3 depicts a computer system 301 operable as server 150 consistent with some embodiments. Server 150 may be operated as a service including multiple computers either alone or together. Server 150 may enable convenient, on-demand network access to a shared pool of configurable computing resources. For example, FIG. 5 depicts a series of functional abstraction layers provided by a cloud computing environment 50 capable of hosting server 150. Consequently, one or more patient intervention conflict detections may be handled by one or more layers of a cloud computing environment 50 consistent with some embodiments.

Referring back to FIG. 1, server 150 may operate by handling requests from and providing responses to clients 120 through network 160. Accordingly, server 150 may provide auditing of access by one or more of the clients. For example, server 150 may include a tracking system or ledger of activity recording all data operations of individual clients 120. Server 150 may also record all conflict detection events, for later inspection by one or more of clients 120. Server 150 may also operate by performing data manipulation, insertion, deletion, or otherwise accessing data stored in secure data store 140. The server 150 may also connect to and access non-specific generic data 170. The generic data 170 may be stored outside of the PHPICD 100, such as in a public datastore. The generic data 170 may list various drugs, drug interactions, treatments, treatment interactions, and other relevant potential conflicts. PHPICD 100 may leverage the generic data 170 to identify certain conflicts in a given patient intervention and existing healthcare interventions that are not patient-specific.

Each client 120 may insert, view, update, or delete records it has stored within the secure data store. For example, client 120-1 may have one or more uploaded records 132-1 in secure data store 140. The uploaded records 132-1 may correspond to a subset of records in private data store 130-1. Client 120-2 may have one or more uploaded records 132-2 in secure data store 140. The uploaded records 132-2 may correspond to a subset of records in private data store 130-2. Correspondingly, client 120-$n$ may have one or more uploaded records 132-$n$ in secure data store 140. The uploaded records 132-$n$ may correspond to a subset of records in private data store 130-$n$.

In some embodiments, insertion, viewing, updating, or deleting records may only be performed by program 110 through techniques of secure multi-party computation. Server 150 may implement secure multi-party computation to act as a sole or true client permitted to access secure data store 140 in coordination with each respective client. For example, client 120-1 may wish to access one or more records 132-1 in secure data store 140. To perform the access, split 112-2 executed by client 120-1 may operate in concert with split 112-1 executed by server 150 to perform access operations of program 110. No other program splits (e.g., 112-3, 112-4) may operate either alone or in combination to perform access operations on records 132-1; only the combination of split 112-2 and split 112-1. Likewise, records 132-2 may only be accessed by a combination of split 112-3 and split 112-1, and records 132-$n$ may only be accessed by a combination of split 112-4 and split 112-1.

Server 150 may also implement secure multi-party computation to act as a sole or true client to perform conflict detection of private patient interventions, consistent with some embodiments. For example, server 150 may be embodied in the form of a garbled circuit that permits full featured entity resolution and relationship detection to be performed through a cooperative computation without revealing data inputs of the clients 120 to effectuate conflict detection. Entity resolution/relationship detection may be embodied in multi-party computation such that all of the splits 112-1, 112-2, 112-3, and 112-4 are required to participate in computations. In some embodiments, program 110 may be embodied such that a majority of splits 112 may operate to perform conflict detection of private patient interventions.

Conflict detection of private patient intervention conflicts performed by system 100 may be based on entity resolution and/or relationship detection. Entity resolution may be performed based on a plurality of rules to determine if two seemingly dissimilar records are in fact the same entity. Relationship detection may be performed by a plurality of rules to determine if two seemingly similar records are actually separate but related entities. Examples of such rules include the following: Two entities with the same last name and the same address or phone number and the same birth date are a single individual. Two entities with the same last name and the same address or phone number in which one's first name is an abbreviation of the other's are a single individual, unless they have different ages, in which case they are related. Two entities with the same last name and the same address or phone number and no other shared data are related. Two individuals with the same work phone number are related. The number of rules for entity resolution/relationship detection embedded within program 110 may be, for example, between twelve and forty such rules, but could be any number.

Performing an entity-relation operation as performed by system 100 may include the process that resolves entities and detects relationships within a plurality of stored records. Each of the records may include one or more attributes, and performance of the entity resolution operation may include executing a series of concise rules against the entity received in the request. Performance of the entity-relation operation may also include execution of the rules against other records stored in a secure storage.

Performing an entity-relation operation may include processing of records in three phases: recognize, resolve, and relate. The recognition phase may include validating, optimizing, and enhancing the incoming records. During this recognize phase, the records may be cleansed and attributes may be standardized, as well as performance of data quality checks on records to protect the integrity of an entity database within a secure storage. During entity resolution, attributes within the records may be identified as entities. After the attributes in the records have been cleansed, standardized or enhanced, sophisticated search algorithms may be used to compare the attributes in the incoming record against existing entities in the entity database to determine if they are the same entity. During entity resolution, additional processing may also complete the relationship detection process, which detects relationships between identities and entities and generates alerts for relationships of interest. In some embodiments, scoring may also occur. For example, during entity resolution, it may be determined how closely attributes for an incoming record match the attributes of an existing entity. The results of this computational analysis are scores that may be used to resolve identities into entities and detect relationships between entities.

Figure 2:
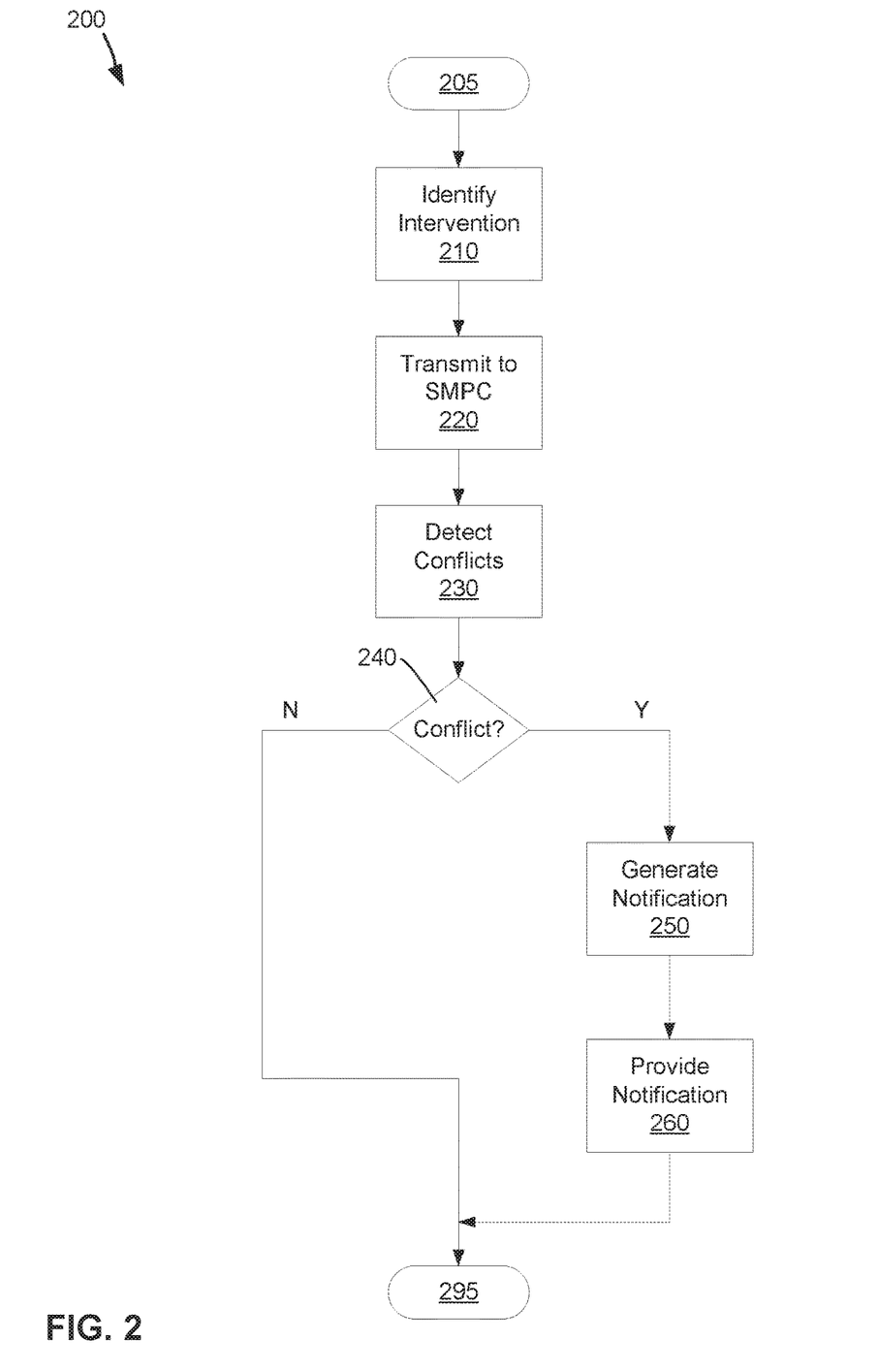
FIG. 2 depicts an example method for performing conflict detection of patient interventions against patient healthcare records, consistent with some embodiments of the disclosure.

FIG. 2 depicts an example method 200 for performing conflict detection of patient interventions against patient healthcare records, consistent with some embodiments of the disclosure. Method 200 may be performed by a PHPICD, such as PHPICD 100 described in FIG. 1. Method 200 may be executed by a computer system, such as a server, desktop computer, or portable computing device. FIG. 3 depicts a computer system 301 operable as a computer system consistent with some embodiments. Method 200 may be provided as a service including multiple computers, either alone or together. Method 200 may be hosted as a workflow from an on-demand network access to a shared pool of configurable computing resources. FIG. 5 depicts a series of functional abstraction layers provide by a cloud computing environment 50 capable of hosting method 200 consistent with some embodiments of the disclosure. Method 200 may be performed repeatedly or continuously, such as every 100 milliseconds or every 16.6 milliseconds. In some embodiments, greater or fewer operations may be performed, or some operations may be combined or performed concurrently.

Referring back to FIG. 2, from start at 205 a first patient intervention may be identified at 210. The first patient intervention may be a treatment, a prescription, or other intervention entered by a healthcare provider into a first patient record of the first patient. For example, a patient may have a medical record with a general practitioner of the patient. The patient may be complaining of back pain, and the general practitioner may assign the patient an intervention of a drug for back pain. Other second patient records may also exist. For example, the patient may have previously visited a physical therapist and the physical therapist may have previously prescribed a drug as a previous or existing patient intervention.

At 220 the first patient intervention may be transmitted to a first program split of an SMPC. For example, the first patient intervention may be identified by a first client. The first client may be software operated by and located at a first healthcare provider. The first client may be a remote client located in a provisioned portion of a cloud-based provider assigned to provide computing resources to the first healthcare provider. The first client may communicate with a secure data store to store, read, and modify patient records in the secure data store of the first healthcare provider. The first program split may be controlled by the first healthcare provider and may not be accessible by any other healthcare provider except for the first healthcare provider, such as through the first client.

At 230 one or more conflicts between the first patient intervention and other patient interventions may be detected. Identifying one or more conflicts can involve comparing the transmitted first patient intervention to existing patient interventions of other healthcare providers in a secure multi-party computation. Identification of conflicts can involve comparing a first patient record provided as part of transmitting the first patient intervention to existent patient records in a secure multi-party computation. Identification of conflicts can also include the comparison of the first patient intervention with a generalized (not patient specific) drug interaction data, such as a drug interaction database (stored either in the ORAM with the other patient records or imported from an outside database and compared inside of the ORAM). Identification of conflicts can also include the comparison of the first patient intervention with a generalized treatment and intervention data such as a medical standards and procedures database (stored either in the ORAM with the other patient records or imported from an outside database and compared inside of the ORAM).

The identification of conflicts in medical interventions can leverage entity-relation operations (entity resolution and relationship detection). For example, a first patient intervention may include a patient name and a prescription name. A relationship detection operation may be performed to identify the patient medical records of the first client, but also of other clients in other medical systems uploaded to the ORAM by other clients. An entity resolution operation may identify that for example "Jay Jessup Smith" is the same as "J. J. Smith" based on other attributes in common (e.g., address). In another example, a first patient intervention may include a patient name, an address, and a medical complaint (e.g., pain, seeking medication). A relationship detection operation may be performed to identify relative medical records of a relative based on the patient name, the address, and another name and address of the relative medical records.

The identification of conflicts can include a series of comparisons based on both multiple comparisons to outside sources (generalized data) and multiple entity-relation operations. For example, a first patient intervention may include the prescription of an antibiotic called ciprofloxacin. The antibiotic medication may have side effects listed regarding tendon damage in athletic participation. The identification of conflicts may include flagging this interaction as a first variable. The identification may next perform an entity resolution operation to identify records located of a second client that indicate the second client was previously prescribed to an intense cardiovascular regimen of exercise and wanted to be cleared to lift weights. The first variable can be matched against the records to identify conflicting interventions in other records; the intense cardiovascular regime intervention being a conflict with the first variable of ciprofloxacin (e.g., an issues with a tendon rupture). The matching can also invoke a list of records in a drug interaction or intervention conflict database that contains generalized (e.g., records that do not have patient-specific entries).

If a conflict was identified (240: Y), then a notification may be generated for the first client at 250. The notification may be generated based on a privacy policy or setting of the client. The notification may be generated based on a regulation or other law that requires the consent or knowledge of the patient. In some embodiments, a first notification may be generated for the first healthcare provider that operates the first client. The first notification may remove any private information, such as by removing any information based on the first patient record. For example, the first patient record may have a series of first patient interventions and other attributes that are located within the first patient record.

The generation of the notification may be performed by removing any data or information that is not located in the first patient records. The removed data may be any information that was located in the second patient records that are in possession or control of an entity that is not the first healthcare provider or the first client. For example, the notification may be "conflict detected with drug." The notification may include a generic description of the conflict. For example, the notification may be "treatment intervention conflict with ciprofloxacin." In another example, the notification may be "drug intervention conflict with warfrin." At 260, the notification may be provided to the first client such that the healthcare provider may be able to adjust the intervention based on the notification.

In some embodiments, a second notification may be generated at 250 and provided at 260 directly to the patient. For example, the notification may be "You have been prescribed ibuprofen, that is a conflict with warfarin." The notification may be delivered to a contact attribute of the patient (e.g., an email address in the first patient record, a text to a phone number in the first patient record). The patient may then act upon the notification by electing to provide the conflict information to the healthcare provider so they can discuss an alternative intervention.

After providing the notification at 260, or after a intervention conflict is not detected at (240:N), method 200 ends at 295.

FIG. 3 depicts the representative major components of an example computer system 301 that may be used, in accordance with some embodiments of the present disclosure. It is appreciated that individual components may vary in complexity, number, type, and/or configuration. The particular examples disclosed are for example purposes only and are not necessarily the only such variations. The computer system 301 may comprise a processor 310, memory 320, an input/output interface (herein I/O or I/O interface) 330, and a main bus 340. The main bus 340 may provide communication pathways for the other components of the computer system 301. In some embodiments, the main bus 340 may connect to other components such as a specialized digital signal processor (not depicted).

The processor 310 of the computer system 301 may be comprised of one or more cores 312A, 312B, 312C, 312D (collectively 312). The processor 310 may additionally include one or more memory buffers or caches (not depicted) that provide temporary storage of instructions and data for the cores 312. The cores 312 may perform instructions on input provided from the caches or from the memory 320 and output the result to caches or the memory. The cores 312 may be comprised of one or more circuits configured to perform one or more methods consistent with embodiments of the present disclosure. In some embodiments, the computer system 301 may contain multiple processors 310. In some embodiments, the computer system 301 may be a single processor 310 with a singular core 312.

The memory 320 of the computer system 301 may include a memory controller 322. In some embodiments, the memory 320 may comprise a random-access semiconductor memory, storage device, or storage medium (either volatile or non-volatile) for storing data and programs. In some embodiments, the memory may be in the form of modules (e.g., dual in-line memory modules). The memory controller 322 may communicate with the processor 310, facilitating storage and retrieval of information in the memory 320. The memory controller 322 may communicate with the I/O interface 330, facilitating storage and retrieval of input or output in the memory 320.

The I/O interface 330 may comprise an I/O bus 350, a terminal interface 352, a storage interface 354, an I/O device interface 356, and a network interface 358. The I/O interface 330 may connect the main bus 340 to the I/O bus 350. The I/O interface 330 may direct instructions and data from the processor 310 and memory 320 to the various interfaces of the I/O bus 350. The I/O interface 330 may also direct instructions and data from the various interfaces of the I/O bus 350 to the processor 310 and memory 320. The various interfaces may include the terminal interface 352, the storage interface 354, the I/O device interface 356, and the network interface 358. In some embodiments, the various interfaces may include a subset of the aforementioned interfaces (e.g., an embedded computer system in an industrial application may not include the terminal interface 352 and the storage interface 354).

Logic modules throughout the computer system 301— including but not limited to the memory 320, the processor 310, and the I/O interface 330—may communicate failures and changes to one or more components to a hypervisor or operating system (not depicted). The hypervisor or the operating system may allocate the various resources available in the computer system 301 and track the location of data in memory 320 and of processes assigned to various cores 312. In embodiments that combine or rearrange elements, aspects and capabilities of the logic modules may be combined or redistributed. These variations would be apparent to one skilled in the art.

It is to be understood that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported, providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure that includes a network of interconnected nodes.

Figure 4:
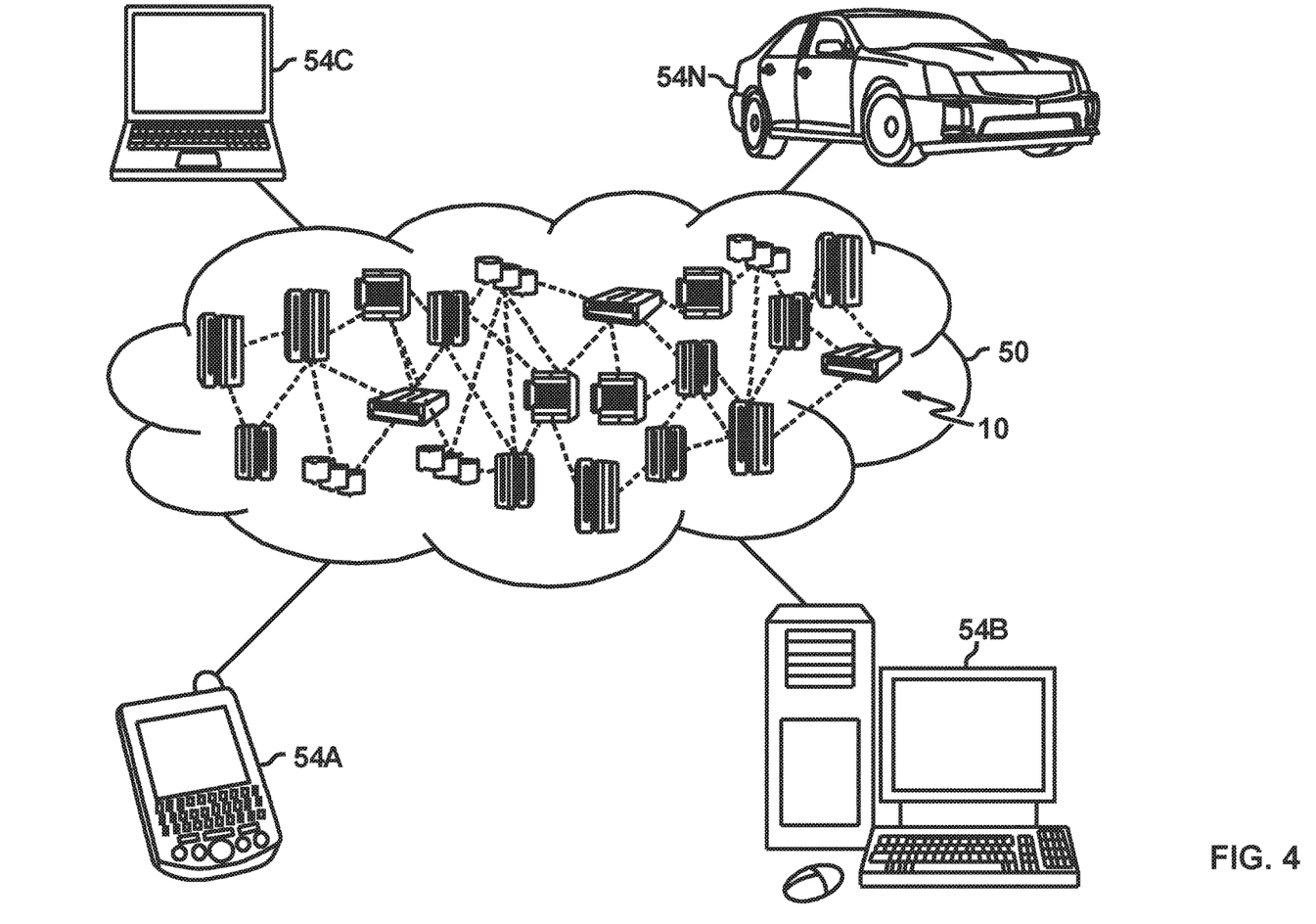
FIG. 4 depicts a cloud computing environment according to an embodiment of the present invention.

Referring now to FIG. 4, illustrative cloud computing environment 50 is depicted. As shown, cloud computing environment 50 includes one or more cloud computing nodes 10 with which local computing devices used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 4 are intended to be illustrative only and that computing nodes 10 and cloud computing environment 50 can communicate with any type of computerized device over any type of network and/or network addressable connection (e.g., using a web browser).

Referring now to FIG. 5, a set of functional abstraction layers provided by cloud computing environment 50 (FIG. 4) is shown. It should be understood in advance that the components, layers, and functions shown in FIG. 5 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may include application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and secure multi party conflict detection of patient interventions 96. For example, a request to perform an entity resolution may be received by one or more clients from portal 83. The request may be passed to a first split (not depicted) of secure multi party conflict detection of patient interventions 96. Conflict detection of patient interventions 96 may, responsively determine, without revealing any of the patient records unowned by the requester the result of the conflict detection back to management layer 80.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be accomplished as one step, executed concurrently, substantially concurrently, in a partially or wholly temporally overlapping manner, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present disclosure have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to explain the principles of the embodiments, the practical application or technical improvement over technologies found in the marketplace, or to enable others of ordinary skill in the art to understand the embodiments disclosed herein.

What is claimed is:

1. A computer-implemented method comprising:
    storing, a first patient record owned by a first client and one or more second patient records owned by a second client, in a secure data store that operates as working memory for hosting a first program split and a second program split, wherein the first patient record and the one or more second patient records are encrypted using a key of a split key technique that enables the first client and the second client to cooperatively recreate the key for decrypting the first patient record and the one or more second patient records, wherein a program is compiled into the first program split and the second program split, where the first program split is operable by the first client and the second program split is operable by the second client, and the first and second program splits are configured to work in concert using a secure multi-party computation to access the first patient record and the one or more second patient records stored in the secure data store using the split key technique, where the first and second program splits cooperatively recreate the key and decrypt the first patient record and the one or more second patient records and perform entity-relation operations and patient intervention conflict detection without revealing unowned patient records to the first and second clients;

receiving from the first client, by the first program split of the secure multi-party computation, a first patient intervention for a first patient with a request to perform a conflict detection of the first patient intervention against the one or more second patient records owned by the second client;

identifying, by the first program split and the second program split of the secure multi-party computation, a second patient record in the one or more second patient records that is associated with the first patient, wherein the first and second program splits operate in concert to recognize, resolve, and relate attributes contained in the first patient record and the one or more second patient records to identify the second patient record associated with the first patient;

detecting, by the first program split and the second program split of the secure multi-party computation, and based on the first patient record and the second patient record, a conflict in the first patient intervention and an existing medical situation regarding the first patient;

generating, by the first program split and based on the conflict, a notification that is related to the conflict; and providing, to the first client and based on the conflict, the notification that is related to the conflict.

2. The method of claim 1, further comprising identifying the first patient intervention by the first client, wherein the first client is operated by a first healthcare provider.

3. The method of claim 2, wherein the one or more second patient records are uploaded to the secure data store by the second program split controlled by the second client, the second client operated by a second healthcare provider, wherein the second client is unable to access any patient records in the secure data store owned by the first client.

4. The method of claim 1, wherein:

the first program split is unable to perform the detecting of the conflict without the second program split.

5. The method of claim 1, wherein:

software is provided as a service in a cloud environment, at least one split of the secure multi-party computation is located on a cloud computer system of a cloud computing service provider, and the secure data store that holds the first patient record is located on the cloud computer system.

6. The method of claim 1, wherein:

the first patient intervention is a first treatment assigned by a first healthcare provider, and the existing medical situation is an existing medical treatment of the first patient.

7. The method of claim 1, wherein:

the first patient intervention is a first treatment assigned by a first healthcare provider, and the existing medical situation is an existing medication assigned to the first patient.

8. The method of claim 1, wherein:

the first patient intervention is a first medication assigned by a first healthcare provider, and the existing medical situation is a second medication previously assigned to the first patient.

9. The method of claim 1, wherein:

the first patient intervention is a first medication assigned by a first healthcare provider, and the existing medical situation is a second medication already assigned to a related person of the first patient.

10. The method of claim 1, wherein:

the first patient intervention is a first medication assigned by a first healthcare provider, and the existing medical situation is an existing treatment assigned to the first patient.

11. A system comprising:

a memory, the memory containing one or more instructions; and a processor, the processor communicatively coupled to the memory, the processor, in response to reading the one or more instructions, configured to:

store, a first patient record owned by a first client and one or more second patient records owned by a second client, in a secure data store that operates as working memory for hosting a first program split and a second program split, wherein the first patient record and the one or more second patient records are encrypted using a key of a split key technique that enables the first client and the second client to cooperatively recreate the key for decrypting the first patient record and the one or more second patient records, wherein a program is compiled into the first program split and the second program split, where the first program split is operable by the first client and the second program split is operable by the second client, and the first and second program splits are configured to work in concert using a secure multi-party computation to access the first patient record and the one or more second patient records stored in the secure data store, where the first and second program splits cooperatively recreate the key and decrypt the first patient record and the one or more second patient records and perform entity-relation operations and patient intervention conflict detection without revealing unowned patient records to the first and second clients;

receive from the first client, by the first program split of the secure multi-party computation, a first patient intervention for a first patient with a request to perform a conflict detection of the first patient intervention against one or more second patient records owned by the second client;

identify, by the first program split and the second program split of the secure multi-party computation, a second patient record in the one or more second patient records that is associated with the first patient, wherein the first and second program splits operate in concert to recognize, resolve, and relate attributes contained in the first patient record and the one or more second patient records to identify the second patient record associated with the first patient;

detect, by the first program split of the secure multi-party computation and by the second program split of the secure multi-party computation, and based on the first patient record and the second patient record, a conflict in the first patient intervention and an existing medical situation regarding the first patient;

generate, by the first program split and based on the conflict detected by the secure multi-party computation, a notification that is related to the conflict; and provide, to the first client and based on the conflict detected by the secure multi-party computation, the notification that is related to the conflict.

12. The system of claim 11, wherein the first client identifies the first patient intervention, and the first client is operated by a first healthcare provider.

13. The system of claim 12, wherein
the one or more second patient records are uploaded to the secure data store by the second client, the second client operated by a second healthcare provider.

14. The system of claim 12, wherein
the one or more second patient records are uploaded to the secure data store by the second program split controlled by the second client, the second client operated by a second healthcare provider.

15. The system of claim 11, wherein:
the first program split is unable to detect the conflict without the second program split, and
the second program split is not accessible by the first client.

16. A computer program product comprising:
one or more computer readable storage media; and
program instructions collectively stored on the one or more computer readable storage media, the program instructions configured to:
store, a first patient record owned by a first client and one or more second patient records owned by a second client, in a secure data store that operates as working memory for hosting a first program split and a second program split,
wherein the first patient record and the one or more second patient records are encrypted using a key of a split key technique that enables the first client and the second client to cooperatively recreate the key for decrypting the first patient record and the one or more second patient records,
wherein a program is compiled into the first program split and the second program split, where the first program split is operable by the first client and the second program split is operable by the second client, and the first and second program splits are configured to work in concert using a secure multi-party computation to access the first patient record and the one or more second patient records stored in the secure data store, where the first and second program splits cooperatively recreate the key and decrypt the first patient record and the one or more second patient records and perform entity-relation operations and patient intervention conflict detection without revealing unowned patient records to the first and second clients;

receive from the first client, by the first program split of the secure multi-party computation, a first patient intervention for a first patient with a request to perform a conflict detection of the first patient intervention against one or more second patient records owned by the second client;

identify, by the first program split and the second program split of the secure multi-party computation, a second patient record in the one or more second patient records that is associated with the first patient, wherein the first and second program splits operate in concert to recognize, resolve, and relate attributes contained in the first patient record and the one or more second patient records to identify the second patient record associated with the first patient;

detect, by the first program split of the secure multi-party computation and by the second program split of the secure multi-party computation, and based on the first patient record and the second patient record, a conflict in the first patient intervention and an existing medical situation regarding the first patient;

generate, by the first program split and based on the conflict detected by the secure multi-party computation, a notification that is related to the conflict; and provide, to the first client and based on the conflict detected by the secure multi-party computation, the notification that is related to the conflict.

17. The computer program product of claim 16, wherein the first client identifies the first patient intervention,
the first client is operated by a first healthcare provider.

18. The computer program product of claim 17, wherein
the one or more second patient records are uploaded to the secure data store by the second client, the second client operated by a second healthcare provider.

19. The method of claim 2, wherein the secure data store operates as an Oblivious Random Access Memory (ORAM).

* * * * *